United States Patent [19]
Dees

[11] Patent Number: 5,789,227
[45] Date of Patent: Aug. 4, 1998

[54] PROCESSING OF CELLULOSIC MATERIAL BY A CELLULASE-CONTAINING CELL-FREE FERMENTATE PRODUCED FROM CELLULASE-PRODUCING BACTERIA, ATCC 55702

[75] Inventor: H. Craig Dees, Lenoir City, Tenn.

[73] Assignee: Lockheed Martin Energy Systems, Inc., Oak Ridge, Tenn.

[21] Appl. No.: 528,178

[22] Filed: Sep. 14, 1995

[51] Int. Cl.$^6$ .............................. C12N 1/20; C12N 9/24; C12N 9/42

[52] U.S. Cl. ...................... 435/209; 435/252.1; 435/200

[58] Field of Search .................................... 435/209, 207, 435/252.34, 263, 264, 822, 200, 252.1; 510/320, 392

[56] References Cited

U.S. PATENT DOCUMENTS

| | | | |
|---|---|---|---|
| 3,616,222 | 10/1971 | Dasinger | 435/105 |
| 4,104,124 | 8/1978 | Srinivasan et al. | 435/110 |
| 4,108,724 | 8/1978 | Nara et al. | 435/74 |
| 4,234,752 | 11/1980 | Skinner et al. | 435/209 |
| 4,388,077 | 6/1983 | Ruck | 8/138 |
| 4,435,307 | 3/1984 | Barbesgaard et al. | 510/305 |
| 4,443,355 | 4/1984 | Murata et al. | 510/320 |
| 4,479,881 | 10/1984 | Tai | 510/322 |
| 4,479,936 | 10/1984 | Vandenbergh et al. | 424/93.47 |
| 4,496,656 | 1/1985 | Nakamura et al. | 435/209 |
| 4,628,029 | 12/1986 | Eveleigh et al. | 435/34 |
| 4,742,005 | 5/1988 | Yamanobe et al. | 435/99 |
| 4,832,864 | 5/1989 | Olson | 8/401 |
| 4,912,056 | 3/1990 | Olson | 435/263 |
| 4,943,532 | 7/1990 | Kawai et al. | 435/209 |
| 4,956,291 | 9/1990 | Yamanobe et al. | 435/200 |
| 4,962,030 | 10/1990 | Kawai et al. | 435/209 |
| 5,006,126 | 4/1991 | Olson et al. | 8/401 |
| 5,122,159 | 6/1992 | Olson et al. | 8/401 |
| 5,213,581 | 5/1993 | Olson et al. | 8/401 |
| 5,231,022 | 7/1993 | Saito et al. | 435/209 |
| 5,314,637 | 5/1994 | Saito et al. | 510/392 |
| 5,318,905 | 6/1994 | Saito et al. | 435/209 |
| 5,340,731 | 8/1994 | Kilburn et al. | 435/179 |
| 5,348,742 | 9/1994 | Howell et al. | 424/93.47 |
| 5,460,966 | 10/1995 | Dixon | 435/263 |

OTHER PUBLICATIONS

G. P. Hazlewood, J. I. Laurie, L. M. A. Ferreira, and H. J. Gilbert, "*Pseudomonas fluorescens* subsp. cellulosa: an alternative model for bacterial cellulase," *Jounral of Applied Bacteriology*, 1992, 72, pp. 244–251.

John Jenkins, Leila Lo Leggio, Gillian Harris, Richard Pickersgill, "β–Glucosidase, β–galactosidase, family a cellulases, family F xylanases and two barely glycanases form a superfamily of enzymes with 8–fold β/α architecture and with two conserved glutamates near the carboxy–terminal ends of β–strands four and seven," *FEBS Letters*, 362(1995), pp. 281–285.

Luis M. Ferreira, Geoffrey P. Hazelwood, Patrick J. Barker, and Harry J. Gilbert, "The celldextrinase from *Pseudomonas fluorescens* subsp. cellulosa consists of multiple functional domains," *Journal of Biochemistry*, vol. 279, No. 3, (1991), pp. 793–800.

H.J. Gilbert, J. Hall, G. P. Hazlewood, and L. M. A. Ferreira, "The N–terminal region of an endoglucanase from *Pseudomonas fluorescens* subspecies cellulosa constitutes a cellulose–binding domain that is distinct from the catalytic centre," *Molecular Microbiology*, vol. 4, No. 5, (1990), pp. 759–768.

Takafumi Yoshikawa, Horoshi Suzuki, and Kazutosi Nisizawa, "Biogenesis of Multiple Cellulase Components of *Pseudomonas fluorescens* var. cellulosa, I. Effects of Culture Conditions on the Multiplicity of Cellulase," *J. Biochem.*, 75, (1974), pp. 531–540.

C. M. G. A. Fontes, J. Hall, B. H. Hirst, G. P. Hazlewood, and H. J. Gilbert, "The resistance of cellulases and xylanases to proteolytic inactivation," *Appl. Microbiol. Biotechnol.* (1995) 43, pp. 52–57.

Jun–Ton Hwang and Hiroshi Suzuki, "Intracellular Distribution and Some Properties of β–Glucosidases of a cellulolytic Pseudomonad," *Agr. Biol. Chem.*, 40 (11), 1976, pp. 2169–2175.

Yuwen Hong, J. J. Pasternak, and Bernard R. Glick, "Purification of *Pseudomonas fluorescens* subsp. cellulosa endoglucanases Produced in *Escherichia coli*," Current Microbiology vol. 20, 1990, Springer–Verlag New York, Inc., pp. 339–342.

Bruce R. Wolff, Diane Lewis, J.J. Pasternak, and Bernard R. Glick, "Partial characterization of *Pseudomonas fluorescens* subsp. cellulosa endoglucanase activity produced in *Escherichia coli*," *Journal of Industrial Microbiology*, 5(1990), pp. 59–64.

Bruce R. Wolff, Bernard R. Glick, and J. J. Pasternak, "DNA sequence analysis of endoglucanase genes from *Pseudomonas fluorescens* subsp. celluslosa and Pseudomonas," *Journal of Industrial Microbiology*, 6(1990), pp. 285–290.

Harry J. Gilbert, Gail Jenkins, Debra A. Sullivan, and Judith Hall, "Evidence for multiple carboxymethylcellulase genes in *Pseudomonas fluorescens* subsp. cellulosa," *M. Gen. Genet* (1987), 210, pp. 551–556.

Craig B. Faulds, Marie–Christine Ralet, Gary Williamson, Geoffrey P. Hazlewood, Harry J. Gilbert, "Specificity of an esterase (XYLD) from *Pseudomonas fluorescens* subsp. cellulosa," *Biochimica et Biophysica Acta*, 1243 (1995), pp. 265–269.

(List continued on next page.)

Primary Examiner—Michael G. Wityshyn
Assistant Examiner—Susan Hanley
Attorney, Agent, or Firm—Preston H. Smirman

[57] ABSTRACT

Bacteria which produce large amounts of a cellulase-containing cell-free fermentate, have been identified. The original bacterium (ATCC 55703) was genetically altered using nitrosoguanidine (MNNG) treatment to produce the enhanced cellulase degrading bacterium ATCC 55702, which was identified through replicate plating. ATCC 55702 has improved characteristics and qualities for the degradation of cellulosic materials.

1 Claim, 5 Drawing Sheets

OTHER PUBLICATIONS

Kunio Yamane, Hiroshi Suzuki, and Kazutosi Nisizawa, "Purification and Properties of Extracellular and Cellbound Cellulase Components of *Pseudomonas fluorescens* var. cellulosa," *The Journal of Biochemistry*, vol. 67, No. 1, 1970, pp. 19–35.

Kunio Yamane, Hiroshi Suzuki, Masao Hirotani, Harumi Ozawa, and Kazutosi Nisizawa, "Effect of Nature and Supply of Carbon Sources on Cellulase Formation in *Pseudomonas flurorescens* var. cellulosa," *The Journal of Biochemistry*, vol. 67, No. 1, 1970, pp. 9–18.

Kunio Yamane, Takafumi Yoshikawa, Hiroshi Suzuki, and Kazutosi Nisizawa, "Localization of Cellulase Components in *Pseudomonas fluorescens* var. cellulosa," *J. Biochem.*, 69 (1971), pp. 771–780.

Bruce R. Wolff, Terry A. Mudry, Bernard R. Glick, and J. J. Pasternak, "Isolation of Endoglucanase Genes from *Pseudomonas fluorescens* subsp. cellulosa and a Pseudomonas sp.," *Applied and Environmental Microbiology*, Jun. 1986, pp. 1367–1369.

André Lejeune, Douglas E. Eveleigh, and Charles Colson, "Expression of an endoglucanase gene of *Pseudomonas fluorescens* var. cellulosa in *Zymomonas mobilis*," *Federation of European Microbiological Societies Letters*, 49 (1988), pp. 363–366.

Louise E. Kellet, Debbie M. Poole, Luis . A. Ferreira, Alastair J. Durrant, Geoffrey P. Hazlewood, and Harry J. Gilbert, "Xylanase B and an arabinofuranosidase from *Pseudomonas fluorescens* subsp. cellulosa contain identical cellulose–binding domains and are encoded by adjacent genes," *Biochemical Journal*, vol. 272, No. 2, (1990), pp. 369–376.

Jane E. Rixon, Luis M. A. Ferreira, Alastair J. Durrant, Judith I. Laurie, Geoffrey P. Hazlewood, and Harry J. Gilbert, "Characterization of the gene celD from *Pseudomonas fluorescens* subsp. cellulosa," *Biochemical Journal*, vol. 285, (1992), pp. 947–955.

Luis M. A. Ferreira, Thomas M. Wood, Gary Williamson, Craig Faulds, Geoffrey P. Hazlewood, Gary W. Black, and Hary J. Gilbert, "A modular esterase from *Pseudomonas fluorescens* subsp. cellulosa contains a noncatalytic cellulose–binding domain," *Biochemical Journal*, vol. 294, (1993), pp. 349–355.

Harry J. Gilbert, Debra A. Sullivan, Gail Jenkins, Louise E. Kellett, Nigel P. Minton, and Judith Hall, "Molecular Cloning of Multiple Xylanase Genes from *Pseudomonas fluorescens* subsp. cellulosa," *Journal of General Microbiology* (1988), 134, pp. 3239–3247.

André Lejeune, Stéphane Courtois, and Colson, "Characterization of an Endoglucanase from *Pseudomonas fluorescens* subsp. cellulosa Produced in *Escherichia coli* and Regulation of the Expression of Its Cloned Gene," *Applied and Enviromental Microbiology*, Feb. 1988, pp. 302–308, vol. 54, No. 2.

André Lejeune, Véronique Dartois, and Charles Colson, "Characterization and expression in *Escherichia coli* of an endoglucanase gene of *Pseudomonas fluorescens* subsp. cellulosa," *Biochimica et Biophysica Acta*, 950 (1988), pp. 201–214.

D. J. Gomes, J. Gomes, W. Steiner, "Production of highly thermostable xylanase by a wild strain of thermophilic fungus *Thermoascus aurantiacus* and partial characterization of the enzyme," *Journal of Biotechnology*, 37 (1994), pp. 11–22.

C. Dees, C. D. Scott, and T. C. Scott, "Partial Characterization of an Inducible Amylase Produced by *Pseudomonas cellulosa*," *Applied Biochemistry and Biotechnology*, vol. 50 (1995), pp. 243–250.

C. Dees, D. Ringelberg, T. C. Scott, and T. J. Phelps, "Characterization of the Cellulose–Degrading Bacterium NCIMB 10462," *Applied Biochemistry and Biotechnology*, vol. 51/52 (1995), pp 263–274.

T. C. Scott, J. M. Cosgrove, C. L. Coon, J. A. Kenney, and C. D. Scott, "Use of Cellulase from *Pseudomonas fluorescens* for the Hydrolysis of Waste Paper in an Attrition Bioreactor," *Applied Biochemistry and Biotechnology*, vol. 51/52 (1995), pp. 537–543.

Miller, "Experiment 14, Nitrosoguanidine Mutagenesis," *Experiments in Molecular Genetics*, 1975, pp. 125–129. publisher: Coldstream Harbor; NY.

Judith Hall, Gary W. Black, Luis M. A. Ferreira, Sarah J. Millward–Sadler, Bassam R. S. Ali, Geoffrey P. Hazlewood, and Harry J. Gilbert, "The non–catalytic cellulose–binding domain of a novel cellulase from *Pseudomonas fluorescens* subsp. cellulosa is important for the efficient hydrolysis of Avicel," *Biochem. J.* (1995) 309, pp. 749–756.

5,789,227

PROCESSING OF CELLULOSIC MATERIAL BY A CELLULASE-CONTAINING CELL-FREE FERMENTATE PRODUCED FROM CELLULASE-PRODUCING BACTERIA, ATCC 55702

This invention was made with Government support under contract DE-AC05-84OR21400 awarded by the U.S. Department of Energy to Lockheed Martin Energy Systems, Inc. and the Government has certain rights in this invention.

FIELD OF THE INVENTION

The present invention relates generally to the conversion of cellulosic materials into fuels, sugars, and specialty chemicals, and more particularly to bacteria which produce cellulase and other enzymes under various environmental conditions.

BACKGROUND OF THE INVENTION

Space in industrial and domestic land fills is becoming increasingly scarce. Therefore, there is need to conserve the space in the existing land fills by reducing the volume of materials via recycling, incineration or other methods. Waste disposable cellulosic materials (i.e., newsprint, diapers, packaging, containers, etc.) are major contributors of the total volume placed in land fill sites. Cellulosic materials are generally defined as those materials which contain cellulose. Cellulose is generally defined as a polymer of β-D-glucose units. Concern over the environmental consequences of depositing these materials has led some environmentally conscious consumers to refrain from purchasing cellulosic disposable items. Major international food suppliers have recently replaced styrofoam packaging materials with more environmentally conscious cellulosic packaging materials. However, a significant volume of cellulosic based materials will still need to be deposited in land fills. Therefore, new methods to enhance the biodegradation of cellulosic materials are required in order to alleviate this problem. New strains of bacteria with genetically enhanced capabilities need to be produced to make these processes commercially feasible.

Additionally, with the increasing dependance on unreliable fossil fuel sources, biomass conversion of waste cellulosic products into alternative fuels is also an area of intense interest. Waste cellulose, coal, or other cellulosic materials can be converted into products that can be used to produce alternative fuels, such as ethanol.

Cellulosic waste streams and fossil fuels often contain hazardous materials besides the cellulosic products. To degrade these materials, expansion of the metabolic capabilities of cellulose degrading organisms are required. Efficient modification of these bacteria will probably require recombinant DNA methods. Stable cloning hosts with characteristics desirable for rapid expression and selection of recombinants are required (i.e., sensitivity to common antibiotics).

Cellulosic waste streams, paper production processes, and fossil fuels often produce extremely harsh environmental conditions. Enhanced organisms with tolerances for extreme environments and relatively low temperature growth are advantageous for bioconversion of cellulosic materials. Conditions for forming bioreactor solid matrices are often very harsh (i.e., very basic pH values). Organisms with enhanced cellulase producing capabilities that can tolerate alkaline conditions are advantageous for use in bioreactors for converting cellulose waste or fossil fuels.

Most efforts on cellulose degrading microorganisms has centered on the cellulose degrading fungi (i.e., *Trichoderma reesei*). However, filamentous fungi are more difficult to grow in a fermentor than a bacterial cellulose degrader. Fungi are more difficult than bacteria to genetically engineer (utilizing recombinant DNA methods) to enhance cellulase production or to modify metabolic capabilities.

Most efforts on bacterial cellulases have been concentrated on the anaerobic cellulose degrading bacteria. However, airless fermentations are more difficult and expensive than those performed with aerobic (air utilizing or air tolerant) bacteria. Many bacteria and fungi produce cellulases that: (1) are not efficiently excreted into the surrounding growth medium, or (2) cannot efficiently degrade solid cellulosic materials. Chemical modification of cellulosic waste is often required to make many solid cellulosic materials available for biodegradation. Thermophilic (requiring high temperatures) cellulose degraders are also of intense scrutiny for use as producers of alternative fuels.

To make bioreactor conversion of waste commercially practical, new genetically enhanced organisms are also required. Additionally, to effectively utilize recombinant DNA methods (genetic engineering) to modify these organisms, acceptable cellulase producing cloning hosts are also required.

Therefore, there is a need for bacteria which produce large amounts of cellulase and other enzymes under various environmental conditions.

OBJECTS OF THE INVENTION

Accordingly, it is an object of the present invention to provide a new and improved bacterium with increased enzyme producing ability.

It is another object of the present invention to provide a new and improved bacterium with increased cellulase producing ability.

It is another object of the present invention to provide a new and improved bacterial cloning host with increased cellulase producing ability.

It is another object of the present invention to provide a new and improved bacterium with increased enzyme producing ability over a wide pH range.

It is another object of the present invention to provide a new and improved bacterium with increased cellulase producing ability over a wide pH range.

It is another object of the present invention to provide a new and improved bacterial cloning host with increased cellulase producing ability over a wide pH range.

It is another object of the present invention to provide a new and improved bacterium with increased enzyme producing ability over a wide temperature range.

It is another object of the present invention to provide a new and improved bacterium with increased cellulase producing ability over a wide temperature range.

It is another object of the present invention to provide a new and improved bacterial cloning host with increased cellulase producing ability over a wide temperature range.

It is another object of the present invention to provide a new and improved bacterium with increased enzyme producing ability over a wide salt range.

It is another object of the present invention to provide a new and improved bacterium with increased cellulase producing ability over a wide salt range.

It is another object of the present invention to provide a new and improved bacterial cloning host with increased cellulase producing ability over a wide salt range.

3

It is another object of the present invention to provide a new and improved bacterium with increased enzyme producing ability and the ability to tolerate chemical contaminants.

It is another object of the present invention to provide a new and improved bacterium with increased cellulase producing ability and the ability to tolerate chemical contaminants.

It is another object of the present invention to provide a new and improved bacterial cloning host with increased cellulase producing ability and the ability to tolerate chemical contaminants.

It is another object of the present invention to provide a new and improved detergent.

It is another object of the present invention to provide a new and improved method of converting cellulosic materials into fuels.

It is another object of the present invention to provide a new and improved method of converting cellulosic materials into sugars.

Further and other objects of the present invention will become apparent from the description contained herein.

SUMMARY OF THE INVENTION

In accordance with one aspect of the present invention, the foregoing and other objects are achieved by:

a microorganism consisting of ATCC 55703, or a mutant strain thereof possessing substantially all of the identifying characteristics of the microorganism.

In accordance with another aspect of the present invention, the foregoing and other objects are achieved by:

a microorganism consisting of ATCC 55702, or a mutant strain thereof possessing substantially all of the identifying characteristics of the microorganism.

In accordance with another aspect of the present invention, the foregoing and other objects are achieved by:

a cellulase produced by a microorganism consisting of ATCC 55703, or a mutant strain thereof possessing substantially all of the identifying characteristics of the microorganism.

In accordance with another aspect of the present invention, the foregoing and other objects are achieved by:

a cellulase produced by a microorganism consisting of ATCC 55702, or a mutant strain thereof possessing substantially all of the identifying characteristics of the microorganism.

In accordance with another aspect of the present invention, the foregoing and other objects are achieved by:

a method for producing a cellulase, which comprises culturing a cellulase-producing microorganism in a medium, the microorganism consisting of ATCC 55703, or a mutant strain thereof possessing substantially all of the identifying characteristics of the microorganism.

In accordance with another aspect of the present invention, the foregoing and other objects are achieved by:

a method for producing a cellulase, which comprises culturing a cellulase-producing microorganism in a medium, the microorganism consisting of ATCC 55702, or a mutant strain thereof possessing substantially all of the identifying characteristics of the microorganism.

In accordance with another aspect of the present invention, the foregoing and other objects are achieved by:

a composition comprising:

4 a cellulase produced by a microorganism consisting of ATCC 55703, or a mutant strain thereof possessing substantially all of the identifying characteristics of the microorganism; and a cellulosic material.

In accordance with another aspect of the present invention, the foregoing and other objects are achieved by:

a composition comprising:

a cellulase produced by a microorganism consisting of ATCC 55702, or a mutant strain thereof possessing substantially all of the identifying characteristics of the microorganism; and a cellulosic material.

In accordance with another aspect of the present invention, the foregoing and other objects are achieved by:

a method of treating a cellulosic material comprising:

contacting the cellulosic material with an amount of a cellulase produced by a microorganism consisting of ATCC 55703, or a mutant strain thereof possessing substantially all of the identifying characteristics of the microorganism.

In accordance with another aspect of the present invention, the foregoing and other objects are achieved by:

a method of treating a cellulosic material comprising:

contacting the cellulosic material with an amount of a cellulase produced by a microorganism consisting of ATCC 55702, or a mutant strain thereof possessing substantially all of the identifying characteristics of the microorganism.

In accordance with another aspect of the present invention, the foregoing and other objects are achieved by:

a detergent comprising:

a cellulase produced by a microorganism consisting of ATCC 55703, or a mutant strain thereof possessing substantially all of the identifying characteristics of the microorganism;

a surfactant; and a builder.

In accordance with another aspect of the present invention, the foregoing and other objects are achieved by:

a detergent comprising:

a cellulase produced by a microorganism consisting of ATCC 55702, or a mutant strain thereof possessing substantially all of the identifying characteristics of the microorganism;

a surfactant; and a builder.

In accordance with another aspect of the present invention, the foregoing and other objects are achieved by:

a bacterial cloning host consisting of ATCC 55702, or a mutant strain thereof possessing substantially all of the identifying characteristics of said bacterial cloning host.

In accordance with another aspect of the present invention, the foregoing and other objects are achieved by:

an enzyme produced by a microorganism consisting of ATCC 55703, or a mutant strain thereof possessing substantially all of the identifying characteristics of said microorganism.

In accordance with another aspect of the present invention, the foregoing and other objects are achieved by:

an enzyme produced by a microorganism consisting of ATCC 55702, or a mutant strain thereof possessing substantially all of the identifying characteristics of said microorganism.

DETAILED DESCRIPTION

Figure 1:
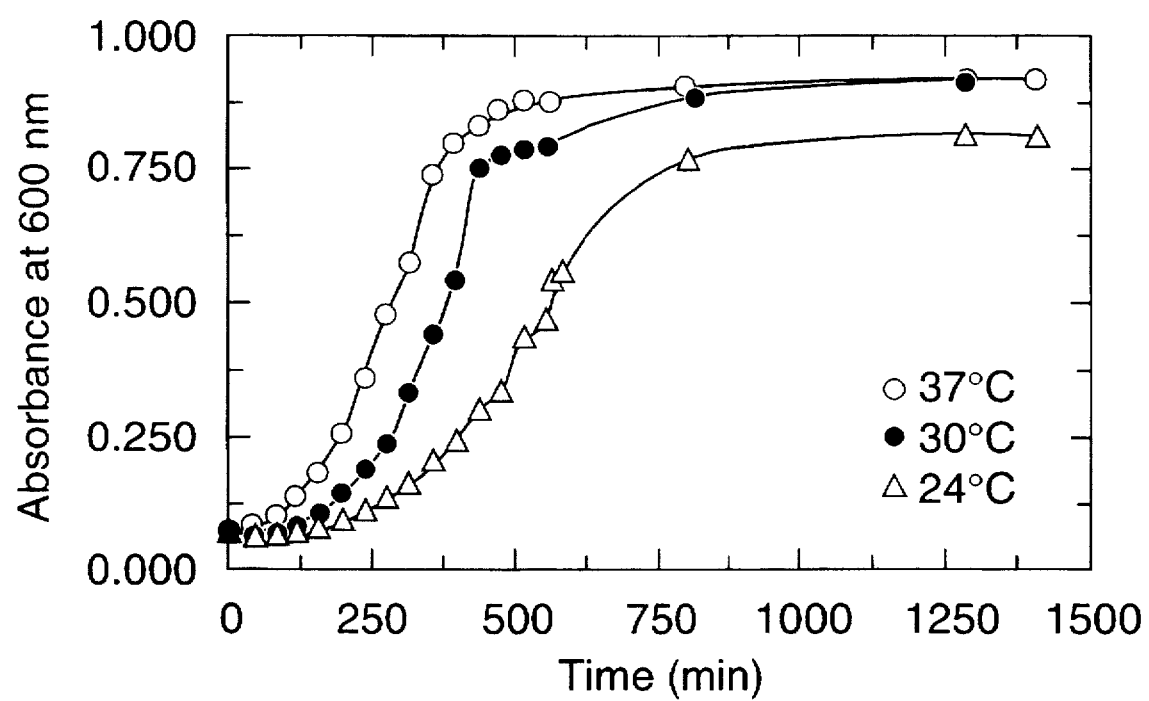
FIG. 1 illustrates a temperature growth curve for the bacteria corresponding to ATCC 55703 and ATCC 55702, in accordance with one aspect of the present invention.

The importance of microorganisms that are capable of producing cellulases has increased with new demands for industrial processes to degrade or modify cellulosic biomass to commercially important materials. The enzymes produced by those microorganisms are not only important in conversion of cellulosic waste to commercially useful feed stocks but also to degrade cellulose and hemicellulose to materials that can be used in the production of alternative fuels. A wide variety of anaerobic and aerobic bacterial cellulase producers have been described including the bacterium NCIB 10462. This organism was originally named *Pseudomonas fluorescens* var. *cellulosa*. The bacterium has also been called *Pseudomonas fluorescens* subsp. *cellulosa* in recent publications. This bacterium was isolated from soil in the early 1950's and was described by Ueda. The bacterium was placed in the National Council for Industrial Bacteriology (hereinafter referred to as NCIB) repository in Scotland, and was given the designation "NCIB 10462." Interest in the study of NCIB 10462 has recently increased along with the recent upsurge of interest in biotechnological conversion of cellulose.

When a sample of NCIB 10462 was recently examined, it was found to have very few identifying characteristics of *Pseudomonas fluorescens* var. *cellulosa*, most noticeably the lack of fluorescence. This led to the conclusion that a new microorganism, which possessed enhanced abilities to produce large amounts of cellulases and other enzymes, had been discovered. The microorganism's original designation has been slightly altered to reflect the lack of fluorescence, and will be currently referred to as *Pseudomonas cellulosa* #28. This designation may be amended at a later time, once sufficient taxonomic studies have been completed. *Pseudomonas cellulosa* #28 was deposited in the American Type Culture Collection (hereinafter referred to as ATCC) and was given Accession No. 55703 (hereinafter referred to as ATCC 55703). ATCC 55703 was then subjected to intense genetic modification using mutagenesis by N-methyl-N'-nitro-N-Nitrosoguanidine (hereinafter referred to as MNNG) treatment. The protocol for this mutagenesis treatment is fully explained in *Experiments in Molecular Genetics*, Miller, pp 125–129 (1972), the entire disclosure of which is incorporated herein by reference. MNNG was utilized because it induces a high frequency of mutations at doses which result in little killing. The resulting microorganism was then designated as Pseudomonas species #142 (or Pseudomonas sp. #142). This microorganism was then deposited in the ATCC and was given Accession No. 55702 (hereinafter referred to as ATCC 55702).

Due to the new importance of these novel bacteria as candidates for commercial biomass conversion, the metabolic and physical properties of ATCC 55703 and ATCC 55702 were examined. ATCC 55703 and ATCC 55702 were examined by utilizing a wide variety of standard bacteriological methods which included assimilation studies, fatty acid analysis, and lipid analysis. ATCC 55703 and ATCC 55702 were found to grow aerobically on a wide variety of solid and soluble cellulosic materials. ATCC 55703 and ATCC 55702 grew in complex medium under reducing conditions and weakly on complex media under full anaerobic conditions. No anaerobic growth was observed in liquid cellulosic medium. Standard bacteriologic identification methods and assimilation studies suggested that these two bacteria have few characteristics corresponding to the genus/species *P. fluorescens*. Assimilation studies suggested only a low probability match with the genus Sphingomonas.

Metabolic and physical characterization of ATCC 55703 and ATCC 55702 revealed that they were alkalophilic, non-fermentative, gram negative, oxidase positive, motile, cellulose degrading bacteria. The aerobic substrate utilization profile of these bacteria were found to have few characteristics consistent with a classification of *P. fluorescens* with a very low probability match with the genus Sphingomonas. Total phospholipid analysis did not reveal the presence of any sphingolipid produced by these bacteria. ATCC 55703 and ATCC 55702 were found to grow best aerobically but also grew well in complex media under reducing conditions. ATCC 55703 and ATCC 55702 grew slowly under full anaerobic conditions on complex media and did not grow anaerobically on cellulose media as the sole carbon source. Total fatty acid analysis (MIDI) of ATCC 55703 and ATCC 55702 failed to group these bacteria with any known genus or species (very low probability match with the genus Vibrio). Therefore, until conclusive taxonomic data can be gathered, these bacteria (ATCC 55703 and ATCC 55702) will continue to be designated as belonging to the Pseudomonas genus.

ATCC 55703 and ATCC 55702 were maintained on solid media consisting of M9 liquid medium to which 15 grams per liter agarose had been added along with 0.1% carboxymethyl cellulose (CMC) as the sole carbon source. ATCC 55703 and ATCC 55702 were then transferred to Trypticase soy agar prior to MIDI analysis. Fatty acid analysis by the MIDI system was performed on ATCC 55703 and ATCC 55702 growing anaerobically on 5% sheeps blood agar.

All studies to determine optimal pH and temperature for growth were performed in Trypticase soy agar broth. Cellulosic media consisted of M9 salt solution as previously described. Agar was added to 15 grams per liter for solid media along with soluble cellulosic component (i.e., carboxymethyl cellulose (CMC)) to 0.1% (w/v). Cellulosic liquid media consisted of M9 salt solution to which strips of filter paper or newspaper had been added. Alternatively, Avicell (powder) was added to 0.1% (w/v).

All bacteriologic assays and growth procedures were performed using standard bacteriology techniques, methods and medias. Non-fermentative analysis was performed using an API non-fermentor identification system. MIDI analysis was performed using standard protocols.

Growth studies and non-fermentative analysis indicate that ATCC 55703 and ATCC 55702 are small non-fermentative gram negative rod bacteria with few characteristics that are typically associated with *P. fluorescens* or even with the genus Pseudomonas. Specifically, Table 1, below, illustrates the similarities and differences between ATCC 55703 and ATCC 55702 with respect to *P. fluorescens* regarding standard biochemical assays:

TABLE 1

| Test | P. fluorescens | ATCC 55703 and ATCC 55702 |
|---|---|---|
| Growth on Blood Agar | + | − |
| Growth on McConkys Agar | + | − |
| Growth in Pseudomonas M10 Medium | + | − |
| Catalase | Strong Positive | Weak Positive |
| Growth in Thioglycollate | Aerobic | Anaerobic |
| Fluorescent | + | − |
| Oxidase | + | + |
| Tryptophanase | − | − |
| Arginine dihydrolase | + | − |
| Urease | − | − |
| Esculin | − | + |
| Gelatinase | + | − |
| PNGP | − | + |
| Glucose | + | + |
| Arabinose | + | + |
| Mannose | + | − |
| n-Acetyl-Glucosamine | + | + |
| Maltose | − | + |
| Gluconate | + | − |
| Caprate | + | − |
| Adipate | + | − |
| Malate | + | − |
| Phenylacetate | ± | − |

Table 2, below, illustrates various morphological and biochemical characteristics of both ATCC 55703 and ATCC 55702:

TABLE 2

| | |
|---|---|
| Gram Morphology | Small gram negative rod approximately 0.5 µm |
| Motility | Motile at 25 and 37° C. |
| Starch Hydrolysis (amylase) | Positive for starch hydrolysis |
| β-galactosidase | Positive |
| β-glucosidase | Positive |
| Hemicellulase | Positive |
| Xylanase | Positive |
| Optimal Growth Temperature (complex media) | 30–37° C. |
| Optimal pH (complex media) | pH 7.2–8.0 |
| Anaerobic growth (37° C.) | |
| Blood Agar | Positive |
| Trypticase Soy Broth | Positive |
| CMC Liquid Medium | Negative |
| CMC Solid Medium | Negative |
| Avicel Liquid Medium | Negative |
| Filter Paper Liquid Medium | Negative |
| Aerobic Growth on Cellulosic Media* | |
| CMC | Positive (solid and liquid) |
| Avicel | Positive (solid and liquid) |
| Filter paper | Positive (solid) |
| Cellobiose | Positive (solid) |
| Newspaper | Positive (liquid) |
| Cellulose acetate | Positive (liquid) |
| Nitrocellulose | Negative (liquid) |
| Polyacrylamide | Negative (liquid) |
| Growth on Other Media (by ATCC 55702 only) | |
| 20% v/v Furfurol | Positive |
| 20% v/v Cinnimyl Alcohol | Positive |
| 20% v/v Saccharinic Acid | Positive |

*Standing or shake cultures at 30 or 37° C.

ATCC 55703 and ATCC 55702 can utilize a wide variety of solid and soluble cellulosic media as a sole carbon source which is consistent with previous observations. ATCC 55703 and ATCC 55702 are oxidase and catalase positive, motile, and aerobic, which are the few characteristics that suggest it might be related to the Pseudomonads. ATCC 55703 and ATCC 55702 only weakly clot a lymulus lysate test which is interesting since they appear to be 0.5–1 µm gram negative rods using gram stain. These studies show that ATCC 55703 and ATCC 55702 are not closely related to the genus Pseudomas, but may have a very low probability match to the genus Sphingomonas.

Table 3, below, illustrates additional biochemical characteristics of ATCC 55703:

TABLE 3

| | |
|---|---|
| Indole Production | Negative |
| N-acetyl glucosaminidase | Positive |
| α-Glucosidase | Positive |
| α-Arabinosidase | Positive |
| β-Glucosidase | Positive |
| α-Fucosidase | Negative |
| Phosphatase | Negative |
| α-Galactosidase | Positive |
| β-Galactosidase | Negative on An-Ident* |
| Indoxyl-acetate hydrolysis | Positive |
| Arginine Utilization | Negative |
| Leucine aminopeptidase | Positive |
| Proline aminopeptidase | Positive |
| Pyroglutamic acid arylamidase | Negative |
| Tyrosine aminopeptidase | Negative |
| Arginine aminopeptidase | Positive |
| Alanine aminopeptidase | Positive |
| Histidine aminopeptidase | Positive (weak) |
| Phenylalanine aminopeptidase | Positive |
| Glycine aminopeptidase | Positive |

*Colonies of ATCC 55703 and ATCC 55702 are positive for β-galactosidase after incubation with X-gal With reference to FIG. 1, the growths of ATCC 55703 and ATCC 55702 at various temperatures are illustrated. ATCC 55703 and ATCC 55702 have an operating temperature range of 5°–37° C., a preferred temperature range of 25°–32° C., and an optimal temperature of 30° C. No growth of ATCC 55703 or ATCC 55702 has been observed at 45° C. With respect to the cellulase produced by ATCC 55703 and ATCC 55702, the operating temperature range is 5°–70° C. (at pH 7.5). The preferred temperature is 55° C. (at pH 7.5).

Figure 2:
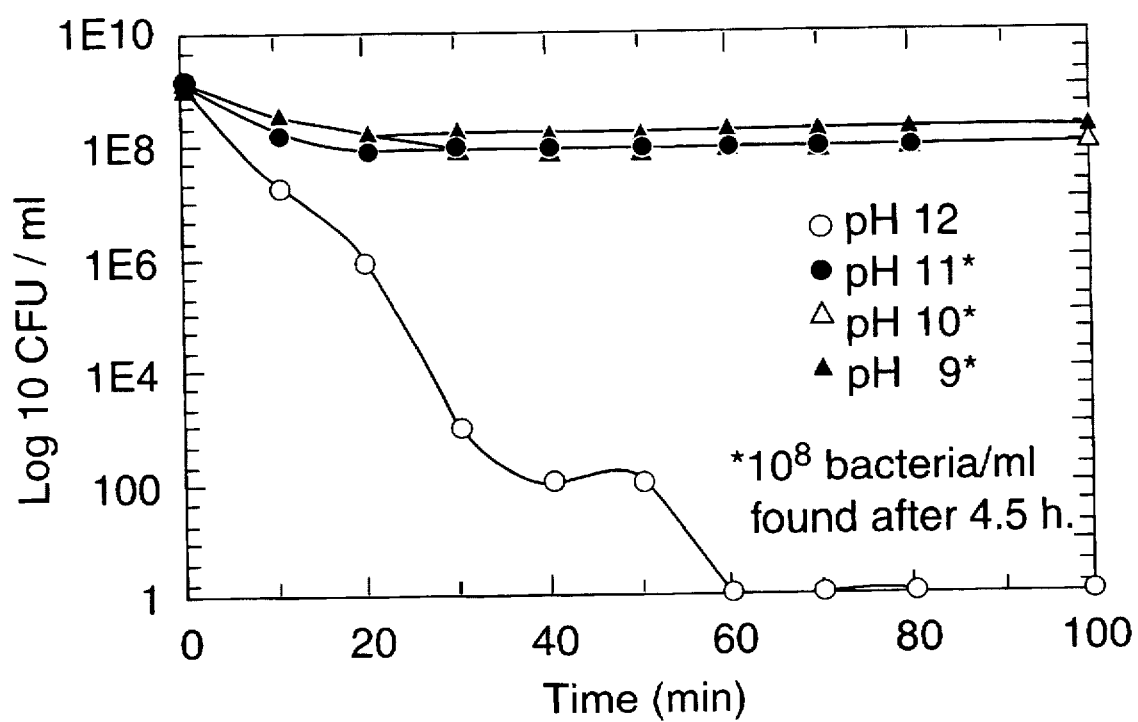
FIG. 2 illustrates a pH stability curve for the bacteria corresponding to ATCC 55703 and ATCC 55702, in accordance with one aspect of the present invention.

With reference to FIG. 2, ATCC 55703 and ATCC 55702 have an operating pH range of 6.8 to 9.0, a preferred pH range of 7.2 to 8.0, with growth decreasing after the pH is adjusted below pH 7.0. In complex media, ATCC 55703 and ATCC 55702 reduced the medium pH below pH 6.8, whereas in liquid cellulosic medium the pH does not fall more than 0.3 from the starting pH of 7.2. With respect to the cellulase produced by ATCC 55703 and ATCC 55702, the operating pH range is 5–11 (at 55° C.). The preferred pH range is 7–8 (at 55° C.).

Figure 3:
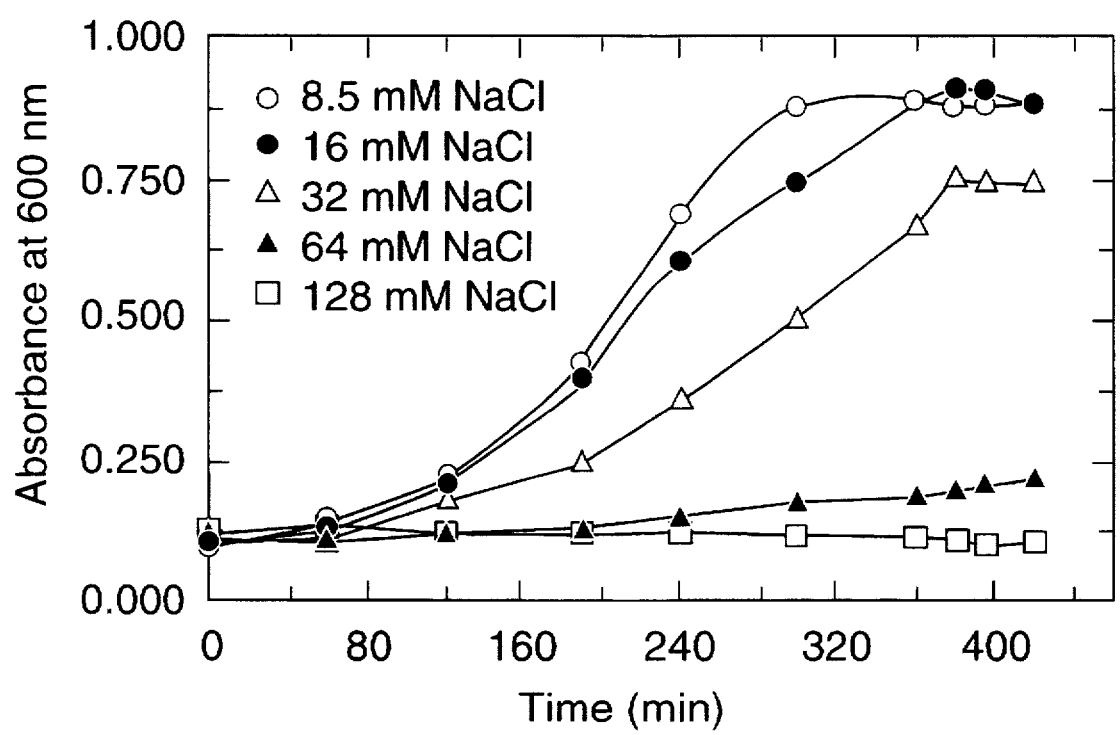
FIG. 3 illustrates a salt tolerance growth curve for the bacteria corresponding to ATCC 55703 and ATCC 55702, in accordance with one aspect of the present invention.

With reference to FIG. 3, the salt tolerance curve illustrates that ATCC 55703 and ATCC 55702 have increased tolerance to twice as much sodium than is commonly used in growth medium. With reference to FIG. 3, ATCC 55703 and ATCC 55702 have an operating salt range of 8.5–32 mM sodium, with a preference of 8.5 mM sodium. Less dilution of high salt brines used in paper processing will be required to use ATCC 55703 and ATCC 55702 to biodegrade cellulosic waste from the paper industry.

Taxonomic characterization of ATCC 55703 and ATCC 55702 using total fatty acid analysis failed to group these bacteria with any of the currently recognized genera. Since the non-fermentative analysis suggested that ATCC 55703 and ATCC 55702 may be distantly related members of the genus Sphingomonas, a total lipid analysis was also performed on ATCC 55703 and ATCC 55702. Results indicated that no sphingolipid is produced by ATCC 55703 or ATCC 55702 and the predominant phospholipids are acyl-linked glycerophosphatides.

Since aerobic substrate utilization studies suggested that ATCC 55703 and ATCC 55702 might have a very low probability match to the genus Sphingomonas, we examined the lipids produced by ATCC 55703 and ATCC 55702 with a special interest in the production of sphingolipid. The lipid profiles of ATCC 55703 and ATCC 55702 are unremarkable. The polar lipid fractions were comprised of ester-linked acyl-glycerophophatides, which would rule out classification of ATCC 55703 or ATCC 55702 in the genus Sphingomonas.

Total fatty acid profiling has been used to identify anaerobic and aerobic bacteria. Total fatty acid analysis failed to adequately group ATCC 55703 or ATCC 55702 into any known genus. Only a low probability match with the genus Vibrio was obtained. Total fatty acid analysis found that a large percentage of the fatty acids produced by ATCC 55703 and ATCC 55702 are in the trans configurations which is characteristic of some members of Vibrio. Ribosomal phylogenetic analysis will probably more closely define the taxonomic position of these bacteria.

Figure 4:
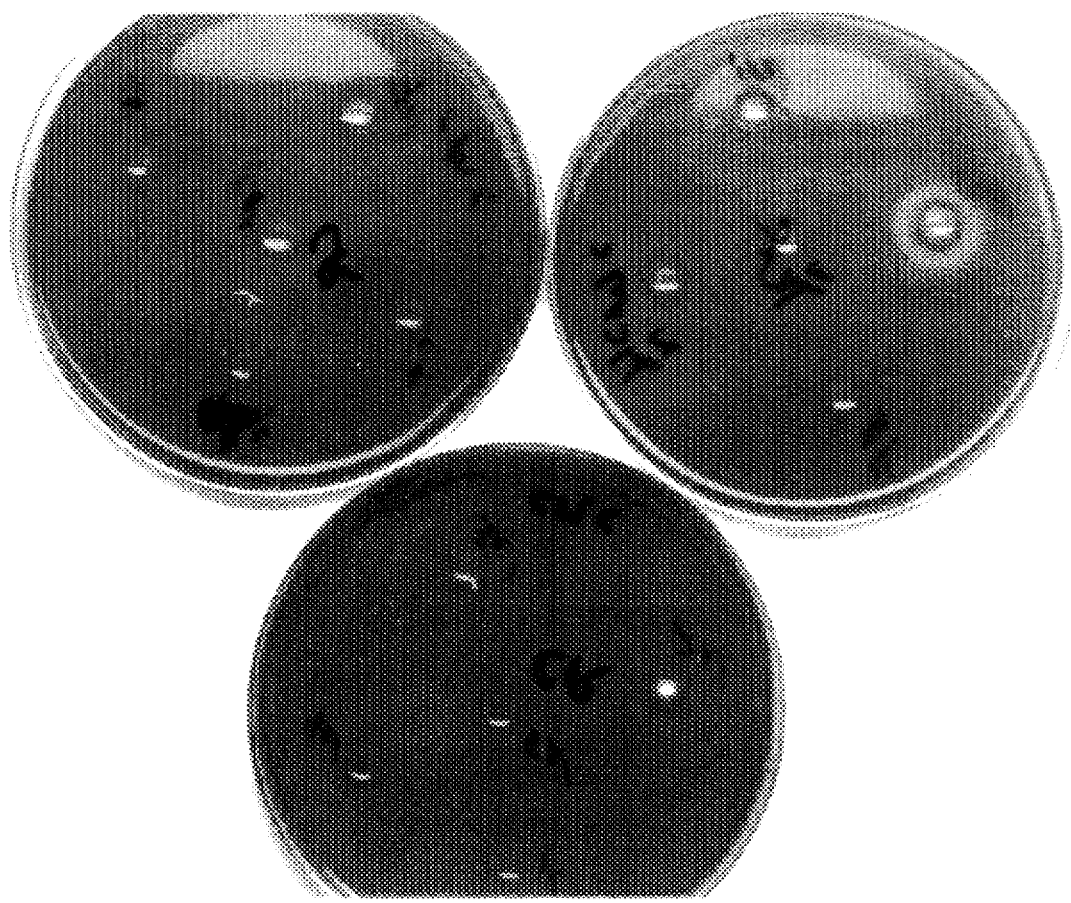
FIG. 4 illustrates a comparison of cellulase (CMCase) activity in culture supernatants of the bacterium corresponding to ATCC 55702 compared to the bacterium corresponding to ATCC 55703, in accordance with one aspect of the present invention.

Both ATCC 55703 and ATCC 55702 are capable of degrading a wide variety of soluble and solid cellulosic materials. Specifically, ATCC 55703 and ATCC 55702 have improved characteristics and qualities for the degradation of cellulosic waste, degradation of cellulosic fossil fuels (i.e., coal) for alternative fuel production, detergents, drain pipe cleaners, septic tank cleaners/additives, textile processing, and paper processing. However, ATCC 55702 has demonstrated a far greater ability to produce large amounts of cellulase than ATCC 55703. FIG. 4 shows that the production of extracellular cellulase from ATCC 55702 is approximately 300 times higher than ATCC 55703. After 24 hours, the zone of clearing around the well of ATCC 55702 is very large (upper right hand corner) (arrow) compared to ATCC 55703 or eleven other cellulase degrading bacteria (no zones visible). Table 4, below, illustrates that ATCC 55702 is superior in (1) production of cellulase, (2) degradation of solid cellulose, and (3) conversion of solid cellulase to sugars when compared to 11 other cellulose degrading bacteria isolated from termite gut. ATCC 55702 is superior in: (1) time to degrade solid cellulose substrates; (2) total sugars produced from common cellulosic wastes (i.e., newsprint); and (3) extracellular endocellulase activity.

TABLE 4

| Species | Filter Paper Degradation (Days)* | Extracellular Cellulase (mm) (Day 5)** | Total Carbohydrate (µg/ml)**** |
|---|---|---|---|
| ATCC 55702 | 3 | 12 | 36.5 |
| Species 1*** | >7 | 0 | 0 |
| Species 2 | >7 | 0 | 0 |
| Species 3 | >7 | 0 | 0 |
| Species 4 | 4 | 0 | 18.1 |
| Species 5 | >7 | 0 | 0 |
| Species 6 | >7 | 0 | 0 |
| Species 7 | >7 | 0 | 0 |
| Species 8 | 6 | 0 | 0 |
| Species 9 | >8 | 0 | 0 |
| Species 10 | >8 | 0 | 0 |
| Species 11 | 6 | 0 | 0 |

*First appearance of filter paper structure is degrading
**Plate diffusion assay zone based on CMC hydrolysis
***Strains isolated from termite gut and include Bacillus sp., Pseudomonas sp., and Flavobacterium sp.-like
****Total carbohydrate in culture supernatants after 5 days growth on newspaper It has also been found that for ATCC 55702 to grow rapidly on solid cellulose and produce the highest amounts of extracellular endocellulase, it must also demonstrate high levels of β-glucosidase (cellobiase) activity. This enzyme converts cellobiose to glucose. ATCC 55702 rapidly produces a colored product from X-GLU (a synthetic marker/test for β-glucosidase production). Therefore, ATCC 55702 is enhanced not only in the production of extracellular cellulases (endoglucanases), but is also enhanced for β-glucosidase activity.

ATCC 55702 is especially suited to biomass conversion of cellulosic waste for alternative fuel production. ATCC 55702 grows best and produces cellulases at temperatures lower than 37° C., a temperature most often used to grow most bacteria and fungi. Lower temperature requirements means that the yield from biomass conversion by ATCC 55702 is more suitable for energy production. The energy required to produce the fuel by growing ATCC 55702 at 20°–24° C. is much less than heating the fermentor or bioreactor to 37° C. ATCC 55702 is greatly superior for alternative fuel production as compared to the thermophilic cellulose degrading bacteria whose growth requires temperatures ranging from 45°–65° C.

In accordance with one aspect of the present invention, a simple powder containing the cellulase and bacteria can be used as an additive to cellulosic waste (i.e., diapers, tampons, newsprint, etc.). The product would be embodied as an inexpensive dried or lyophilized powder of the total fermentate which contains bacteria and cellulase. No post fermentation ("down stream") processing would be required. The product would only require fermentation, lyophilization or drying, and packaging. Summarizing, the powder could consist alternatively of: (1) dried fermentate (cellulase) plus cells (bacteria); (2) dried cells (bacteria); or (3) dried fermentate (cellulase). Additionally, the product could be packaged in a liquid format. Thus, the liquid product could consist alternatively of: (1) fermentate (cellulase); (2) lysed cells (bacteria); or (3) fermentate (cellulase) plus lysed cells (bacteria).

Introduction of new genetic traits into bacteria are inhibited by the enzymes which repair the genetic material (DNA repair and recombination). Thus, any trait introduced into a bacterium by either classical methods (mutagenesis) or recombinant DNA technologies (genetic engineering) can be destroyed by rearrangement of the genetic material by the DNA enzymes. In the most common cloning vehicle *Escherichia coli*, recombinase deficient cloning hosts have been created that lack these recombinase genes (rec- strains). However, cloning of cellulase genes into *E. coli* is not commercially practical since the organism cannot secrete the cellulase. Further, introduction of cellulase genes is inefficient when compared to bacteria that naturally have the ability to degrade cellulose. Restrictions on the use of recombinant DNA technology to give a new metabolic capability (i.e., cellulase production) to those organisms that do not have it previously, make commercial use of the recombinant bacteria prohibitive. The ideal solution is to enhance the ability of a bacteria that already produces cellulase using standard and recombinant DNA technologies.

Figure 5:
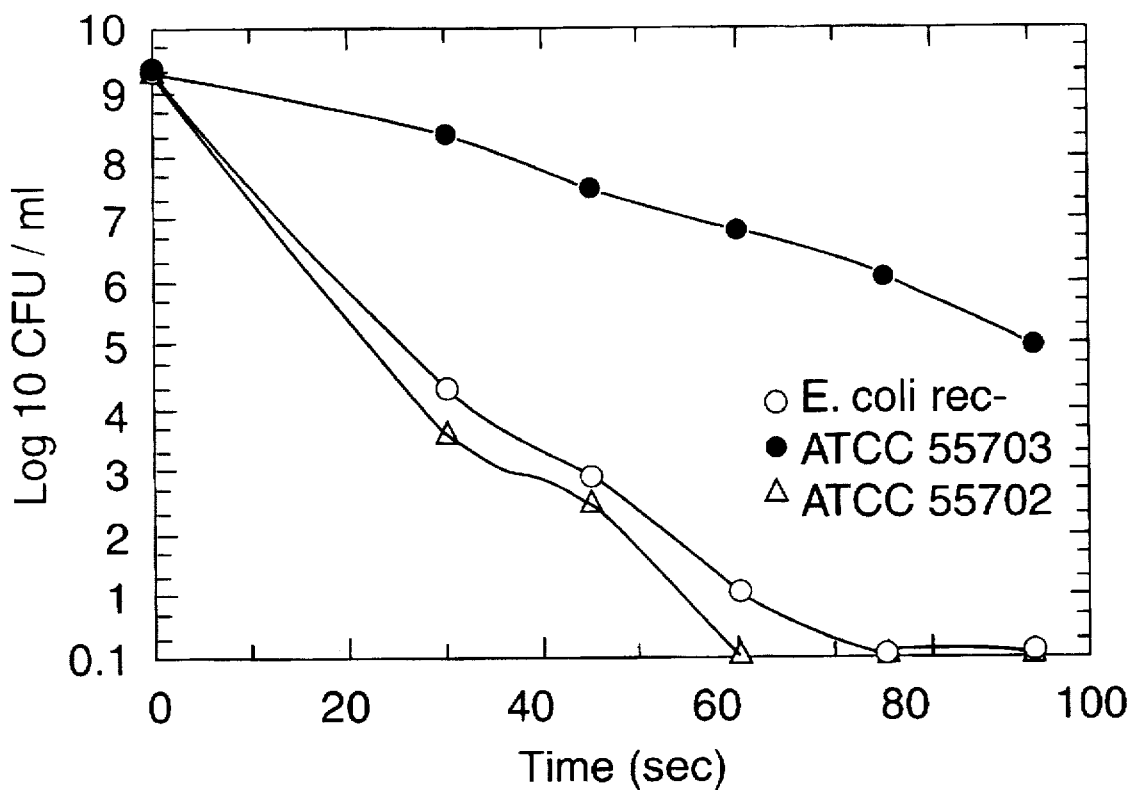
FIG. 5 illustrates an ultraviolet kill curve for a rec-equivalent cellulose degrading bacterium corresponding to ATCC 55702, as compared to an *E. coli* rec- and ATCC 55703, in accordance with one aspect of the present invention.

ATCC 55702 would therefore be an improved host for genetic manipulations using recombinant DNA techniques, and is less likely to destroy genetic manipulations using standard mutagenesis techniques. ATCC 55702 is equivalent to *Escherichia coli* recombinant deficient (rec-). Since reccloning hosts cannot repair or recombine DNA, they are very susceptible to the killing by ultraviolet (UV) irradiation. FIG. 5 illustrates a UV kill curve performed on ATCC 55703, which is UV resistant. Conversely, a rec- *E. coli* cloning host is rapidly killed by slow exposure to UV radiation (FIG. 5). Additionally, the kill curve of ATCC 55702 (a UV sensitive (rec- equivalent) cellulose degrading bacterium) is shown in FIG. 5. Therefore, the ATCC 55702 cloning host will be less able to recombine/repair DNA as efficiently as the wild type bacterium. This feature limits the cloning host from "moving" the genetic elements and destroying them via DNA repair or recombination mechanisms.

Ideal cloning hosts usually require that they be sensitive to two common antibiotics (tetracycline and ampicillin) that are used to select for recombinants. ATCC 55703 was resistant to ampicillin and was partially resistant to tetracycline. Selection via replicate plating during the process of developing the ATCC 55702 rec- strain produced a strain that was also highly sensitive to tetracycline and ampicillin. Therefore, in accordance with one aspect of the present invention, the ATCC 55702 cloning host is highly sensitive to these two antibiotics, which is illustrated in Table 5, below:

TABLE 5

| Antibiotic | 10 μg/ml conc. | 50 μg/ml conc. | 100 μg/ml conc. | 200 μg/ml conc. |
|---|---|---|---|---|
| Streptomycin | s* | s | s | s |
| Tetracycline | r | s | s | s |
| Chloramphenicol | s | s | s | s |
| Ampicillin | r | r | s | s |
| Penicillin G | r | r | r | r |
| Gentamicin | s | s | s | s |

*s = sensitive,
r = resistant

As previously mentioned, ATCC 55703 was subjected to an intensive mutagenesis regimen using MNNG. Resulting strains were selected for: (1) improved soluble cellulase production; (2) rapid degradation of solid cellulose and waste products (filter paper, newsprint and diapers); (3) UV sensitivity; (4) enhanced β-glucosidase activity; (5) tetracycline and ampicillin sensitivity; and (6) high levels of total carbohydrate production from solid cellulose. As a result of replicate plating procedures, ATCC 55702 was identified.

The present invention has many applications with respect to detergents, drain pipe cleaners, septic tank cleaners/additives, conversion of cellulosic materials to animal feedstocks, conversion of starches to sugars, increased lignin and hemicellulose removal from cellulosic materials, textiles, food processing, enzymes, detergents, paper products, bioremediation, specialty chemicals, consumer goods, and renewable fuels.

DEPOSIT OF MICROORGANISMS

The Applicant, in accordance with the provisions of the Budapest Treaty on the International Recognition of the Deposit of Microorganisms for the Purposes of Patent Procedure, did deposit samples of *Pseudomonas cellulosa* #28 and Pseudomonas species #142 with the American Type Culture Collection (ATCC), 12301 Parklawn Drive, Rockville, Md. 20852, United States of America on Aug. 17, 1995 and was assigned accession numbers ATCC 55703 and ATCC 55702, respectively. Both of these microorganisms, namely ATCC 55703 and ATCC 57702, will be irrevocably and without restriction or condition released to the public upon issuance of a patent.

While there has been shown and described what are present considered the preferred embodiments of the invention, it will be obvious to those skilled in the art that various changes and modifications can be made therein without departing from the scope of the invention defined by the appended claims.

What is claimed is:

1. A method of hydrolyzing a cellulosic material, comprising the steps of:

providing a cellulosic material; and hydrolyzing said cellulosic material by contacting said material with an amount of a cellulase-containing cell-free fermentate comprising cellulase sufficient to catalyze the hydrolysis of said cellulosic material, wherein said cellulase-containing cell-free fermentate is produced from the microorganism ATCC 55702, or a mutant strain thereof, possessing all of the identifying characteristics of said microorganism.

* * * * *